(12) United States Patent
Hull

(10) Patent No.: US 12,070,342 B2
(45) Date of Patent: Aug. 27, 2024

(54) INFANT IMMOBILIZER FOR MEDICAL IMAGING

(71) Applicant: University of Kansas, Lawrence, KS (US)

(72) Inventor: Holly Hull, Leawood, KS (US)

(73) Assignee: University of Kansas, Lawrence, KS (US)

( * ) Notice: Subject to any disclaimer, the term of this patent is extended or adjusted under 35 U.S.C. 154(b) by 33 days.

(21) Appl. No.: 17/399,626

(22) Filed: Aug. 11, 2021

(65) Prior Publication Data

US 2022/0047228 A1 Feb. 17, 2022

Related U.S. Application Data

(60) Provisional application No. 63/065,815, filed on Aug. 14, 2020.

(51) Int. Cl.
*A61B 6/04* (2006.01)
(52) U.S. Cl.
CPC ........ *A61B 6/0421* (2013.01); *A61B 2503/04* (2013.01)
(58) Field of Classification Search
CPC ........... A61B 6/00; A61B 6/04; A61B 6/0421; A61B 2503/00; A61B 2503/04
See application file for complete search history.

(56) References Cited

U.S. PATENT DOCUMENTS

| | | | | |
|---|---|---|---|---|
| 3,861,666 A | * | 1/1975 | Nishiyama | A61G 1/01 5/601 |
| 3,933,154 A | * | 1/1976 | Cabansag | A61F 5/3776 378/208 |
| 4,779,858 A | * | 10/1988 | Saussereau | A61B 6/508 5/601 |
| 2003/0131855 A1 | * | 7/2003 | Carter | A61B 6/0421 128/870 |
| 2014/0224262 A1 | * | 8/2014 | Parent | A61B 6/0421 128/878 |

\* cited by examiner

*Primary Examiner* — Fredrick C Conley
(74) *Attorney, Agent, or Firm* — RAY QUINNEY & NEBEKER P.C.; Paul N. Taylor

(57) ABSTRACT

A medical imaging support includes a substantially flat radiotransparent platform, a plurality of radiotransparent flaps, and closure mechanisms. The platform has a longitudinal direction between a top edge and a bottom edge. The plurality of sets of radiotransparent flaps have a first set of the radiotransparent flaps positioned closer to the top edge in the longitudinal direction than the second set of radiotransparent flaps, and at least one set of flaps includes a first flap and a second flap where the first flap is fixed to the platform proximate a first side edge and the second flap is fixed to the platform proximate a second side edge. The closure mechanisms are positioned on the first flap or second flap of each set of radiotransparent flaps, wherein the closure mechanism selectively fixes the first flap to the second flap of each set of radiotransparent flaps.

20 Claims, 4 Drawing Sheets

INFANT IMMOBILIZER FOR MEDICAL IMAGING

PRIORITY CLAIM

The present application claims priority to and the benefit of U.S. Provisional Patent Application No. 63/065,815 entitled INFANT IMMOBILIZER filed Aug. 14, 2020, the disclosure of which is incorporated herein by reference in its entirety.

STATEMENT OF GOVERNMENT INTEREST

This invention was made with government support under Grant No. DK118220, awarded by the National Institutes of Health. The government has certain rights in the invention.

BACKGROUND OF THE DISCLOSURE

Medical imaging is the technique and process of imaging the interior of a body for clinical analysis, as well as visual representation of the function of some organs or tissues. Medical imaging allows clinicians and healthcare provides to view internal structures of the patient's body such as internal organs and bones, as well as to diagnose and treat disease. Medical imaging also allows the clinician and healthcare providers to monitor changes in the patient's body to identify abnormalities or changes in the body.

Medical imaging can include the imaging technologies of X-ray radiography, dual-energy x-ray absorptiometry (DEXA), magnetic resonance imaging (MRI), ultrasound, endoscopy, elastography, tactile imaging, thermography, medical photography, nuclear medicine functional imaging techniques as positron emission tomography (PET) and single-photon emission computed tomography (SPECT).

Such techniques can include exposing the patient's body to a source of particles or radiation that are reflected or transmitted by the patient's body. By measuring the particles or radiation that is reflected or transmitted by the patient's body, a device or system can create images of different structures of the body. The process can require extended periods of time for signal collection, and movement of the patient can introduce artifacts and/or errors into the image. As some techniques expose the patient to undesirable radiation, efficient collection of the signal can reduce the amount of radiation to which the patient is exposed, producing better quality images with less risk to the patient.

SUMMARY

In some embodiments, a medical imaging support includes a substantially flat radiotransparent platform, a plurality of radiotransparent flaps, and closure mechanisms. The platform has a longitudinal direction between a top edge and a bottom edge. The plurality of sets of radiotransparent flaps have a first set of the radiotransparent flaps positioned closer to the top edge in the longitudinal direction than the second set of radiotransparent flaps, and at least one set of flaps includes a first flap and a second flap where the first flap is fixed to the platform proximate a first side edge and the second flap is fixed to the platform proximate a second side edge. The closure mechanisms are positioned on the first flap or second flap of each set of radiotransparent flaps, wherein the closure mechanism selectively fixes the first flap to the second flap of each set of radiotransparent flaps.

In some embodiments, a medical imaging support includes a substantially flat radiotransparent platform, a plurality of radiotransparent flaps, and closure mechanisms. The platform has a longitudinal direction between a top edge and a bottom edge. The plurality of sets of radiotransparent flaps have a first set of the radiotransparent flaps positioned closer to the top edge in the longitudinal direction than the second set of radiotransparent flaps, and at least one set of flaps includes a first flap and a second flap that are a first end and second end of a single piece of radiotransparent material. The closure mechanisms are positioned on the first flap or second flap of each set of radiotransparent flaps, wherein the closure mechanism selectively fixes the first flap to the second flap of each set of radiotransparent flaps.

In some embodiments, a medical imaging support includes a substantially flat radiotransparent platform, a plurality of radiotransparent flaps, and an adjustable tensioning mechanism. The platform has a longitudinal direction between a top edge and a bottom edge. The plurality of sets of radiotransparent flaps have a first set of the radiotransparent flaps positioned closer to the top edge in the longitudinal direction than the second set of radiotransparent flaps, and at least one set of flaps includes a first flap and a second flap where the first flap is fixed to the platform proximate a first side edge and the second flap is fixed to the platform proximate a second side edge. The adjustable tensioning mechanism is connected to at least one flap and is configured to change a tension force on the flap.

This summary is provided to introduce a selection of concepts that are further described below in the detailed description. This summary is not intended to identify key or essential features of the claimed subject matter, nor is it intended to be used as an aid in limiting the scope of the claimed subject matter.

Additional features and advantages of embodiments of the disclosure will be set forth in the description which follows, and in part will be obvious from the description, or may be learned by the practice of such embodiments. The features and advantages of such embodiments may be realized and obtained by means of the instruments and combinations particularly pointed out in the appended claims. These and other features will become more fully apparent from the following description and appended claims or may be learned by the practice of such embodiments as set forth hereinafter.

BRIEF DESCRIPTION OF THE DRAWINGS

In order to describe the manner in which the above-recited and other features of the disclosure can be obtained, a more particular description will be rendered by reference to specific embodiments thereof which are illustrated in the appended drawings. For better understanding, the like elements have been designated by like reference numbers throughout the various accompanying figures. While some of the drawings may be schematic or exaggerated representations of concepts, at least some of the drawings may be drawn to scale. Understanding that the drawings depict some example embodiments, the embodiments will be described and explained with additional specificity and detail through the use of the accompanying drawings in which.

DETAILED DESCRIPTION

Figure 1:
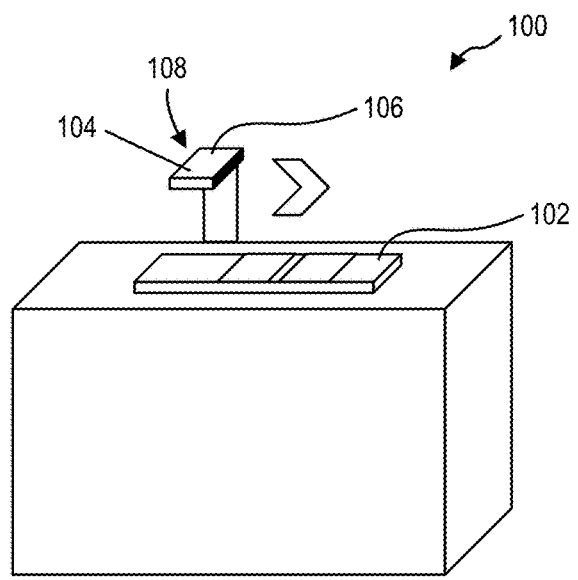
FIG. 1 is a perspective view of a medical imaging system, according to at least one embodiment of the present disclosure.

This disclosure generally relates to devices, systems, and methods for improving image quality in medical imaging of infants or young children. More particularly, the present disclosure relates to radiotransparent devices and systems for limiting the movement of the infant or young child patient during medical imaging of the patient. Movement of the patient can introduce artifacts and/or errors into the image. As some medical imaging techniques expose the patient to undesirable radiation, efficient collection of the signal can reduce the amount of radiation to which the patient is exposed, producing better quality images with less risk to the patient.

In particular, infant and small children imaging is a challenge. Communicating instructions to the infant or small child is generally not possible, and it is desirable to limit the patient's exposure to the imaging radiation or particles due to repeated scans. Collecting the required information in a single scan provides the safest procedure possible for all patients, but particularly for infants and small children.

In some embodiments according to the present disclosure, an immobilizer ensures that infants from ages 2 weeks up to 24 months old remain motionless during a medical imaging scan to assess body composition. The immobilizer is a medical imaging support device, which the infant is placed on. The support includes a plurality of flexible radiotransparent straps and/or flaps that allow a doctor, nurse, clinician, technician, or other user to secure the infant to a radiotransparent platform.

In addition to keeping the infant motionless, the immobilizer may hold the infant in a position that allows appropriate assessment of the scan and assessment of regional adipose tissue distribution. In some embodiments, the immobilizer positions the infant on their back. In some embodiments, the immobilizer includes a head stabilizer that positions the infant's head forward or to either side, depending on the needs of the imaging procedure. For example, the head stabilizer may include a recess in the platform to cradle the infant's head in a desired position. In some embodiments, the immobilizer includes a leg stabilizer, such as an elongated block made of foam or another radiotransparent material. The leg stabilizer may allow for the infant's legs to be safely and comfortably immobilized apart from one another for imaging purposes.

The immobilizer comprises of a series of straps and/or flaps that prevent movement of the infant. The straps are placed above and below joints to immobilize each body segment. The immobilizer is attached to the scan bed, to prevent movement in the vertical plane. In some embodiments, the immobilizer includes at least two sets of a pair of flaps or straps each. Each set of straps is configured to immobilize a portion of the infant's body. In some embodiments, the straps are secured to the platform. In some embodiments, the straps are continuous through a pair of apertures through the platform to allow a single strap to be continuous over the infant and underneath the platform. In such embodiments, the straps may be exchanged for straps of other sizes, providing flexibility in the usage of the immobilizer.

In some embodiments, the flaps or straps are secured to a top surface of the platform. For example, the flaps or straps may be stitched onto the top surface of the platform. In another example, the flaps or straps may be secured to the top surface by a hook and loop mechanism.

In some embodiments, the immobilizer includes 2 sets of flaps that have a closure mechanism to close the set of flaps over the infant. In some embodiments, the immobilizer includes 3 sets of flaps. In some embodiments, the immobilizer includes shoulder straps that are connected to the top edge of the platform and secure the infant over the shoulders. The shoulder straps may connect to a first set of the flaps.

In some embodiments, the flaps or straps include a closure mechanism includes a clip, clasp, buckle, or other mechanical closure mechanism. In some embodiments, the flaps or straps include a hook and loop closure mechanism. In some embodiments, the flaps or straps have an adhesive thereon, and the flaps or straps may be single-use.

FIG. 1 is a perspective view of a medical imaging device 100 with an immobilizer 102 thereon. In some embodiments, such as that illustrated in FIG. 1, the medical imaging device 100 is a dual-energy x-ray absorptiometry (DEXA) imaging device. In some embodiments, the medical imaging device is another type of imaging device, such as x-ray radiography, magnetic resonance imaging (MRI), ultrasound, endoscopy, elastography, tactile imaging, thermography, medical photography, nuclear medicine functional imaging techniques as positron emission tomography (PET) and single-photon emission computed tomography (SPECT).

In some embodiments, the medical imaging device 100 includes a movable energy source 104 and/or a movable signal receiver 106. In some embodiments, the energy source 104 and signal receiver 106 are housed within a movable housing 108, such that the energy source 104 and signal receiver 106 move together. In some embodiments, the energy source 104 and signal receiver 106 are housed in separate housings, but connected to move together along a portion of the patient. The movable energy source 104 and/or a movable signal receiver 106 allow the medical imaging device 100 to selectively image portions of the patient's body at any given time by collecting signal at the current location of the movable energy source 104 and/or a movable signal receiver 106 and subsequently moving to an adjacent imaging location, such as along a length of the patient's body and/or along a length of a patient's limb. As the movable energy source 104 and/or a movable signal receiver 106 move relative to the patient's body, the medical imaging device 100 can align or correlate the signal collected at each imaging location to create a composite image of the composition of the patient's body. In the case of a DEXA system, multiple frequencies of signal are provided and collected, allowing for concurrent imaging of different tissues or materials in the patient's body.

Movement of the patient's body during signal collection at an imaging location or movement of the patient's body during repositioning of the movable energy source 104 and/or a movable signal receiver 106 at a second imaging location can generate errors or artifacts within the collected signal at the imaging location or within the composite image.

Figure 2:
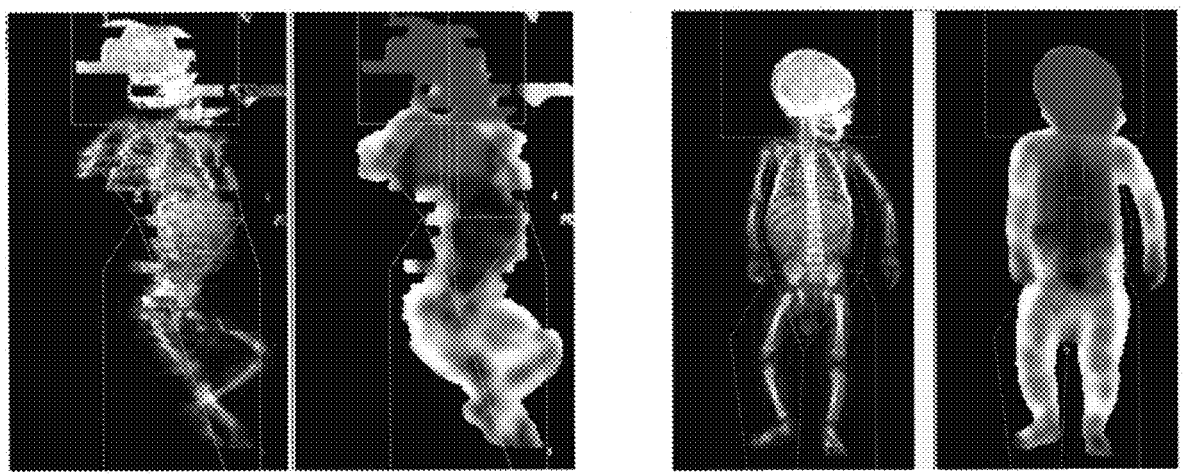
FIG. 2 is a comparison of medical images collected without and with an immobilizer, according to at least one embodiment of the present disclosure.

For example, FIG. 2 illustrates a comparison of a first DEXA composite image collected on an infant that was not immobilized and able to move during the imaging process (in the left images showing bone and soft tissue composition, respectively) and a second DEXA composite image collected on an infant that was immobilized (in the right images) using an immobilizer according to the present disclosure. The first DEXA composite image shows seams between each "slice" of the image, rendering the image unusable for clinical purposes. Each slice of the image can require at least 5 to 6 seconds of imaging time, and the entire image can require at least several minutes of the patient remaining motionless to ensure a usable image. Errors or artifacts within a slice or in the composite image (such as those shown on the left) can necessitate additional imaging of the patient, resulting in unnecessary exposure to radiation or particles. The images on the right show a clear, usable image of a patient immobilized with an immobilizer according to the present disclosure that provides accurate information to the clinician in a single session, which is safer and easier for the infant or small child patient.

In some embodiments, the infant immobilizer is made of or includes radiotransparent material(s). For example, a DEXA imaging system may provide x-ray radiation at a flux of 0.2 millisieverts (mSv). The infant immobilizer is made of or includes radiotransparent materials that are radiotransparent to the flux provided by the medical imaging device. In some examples, a radiotransparent material according to the present disclosure should be understood to transmit at least 50% of the radiation and/or particles provided by and/or collected by the medical imaging device that are incident upon the radiotransparent material. In other examples, a radiotransparent material according to the present disclosure should be understood to transmit at least 75% of the radiation and/or particles provided by and/or collected by the medical imaging device that are incident upon the radiotransparent material. In yet other examples, a radiotransparent material according to the present disclosure should be understood to transmit at least 90% of the radiation and/or particles provided by and/or collected by the medical imaging device that are incident upon the radiotransparent material. In further examples, a radiotransparent material according to the present disclosure should be understood to transmit at least 95% of the radiation and/or particles provided by and/or collected by the medical imaging device that are incident upon the radiotransparent material. In at least one example, a DEXA scan images a child or small patient with approximately 0.00018 Rads of radiation. In at least one embodiment, a radiotransparent material transmits no more than 0.00018 Rads to allow x-ray imaging.

A radiotransparent material may have a range of radiotransmission rates, as the actual radiotransparency is also related to a thickness of the material used in the immobilizer. For example, a bulk material with a high radiotransmission rate may be used in a thicker component of the immobilizer (relative to the direction of signal propagation) than a second material with a lower radiotransmission rate. In at least one example, a platform of the immobilizer is substantially rigid and includes a first radiotransparent material that is thicker than the straps of the immobilizer, which are flexible and include a second radiotransparent material.

In some embodiments, the stabilizer includes a polyethylene foam that contacts the patient and provides cushioning to the patient's body during compression from the straps. The polyethylene foam or other cushioning material allows the straps and/or flaps and platform to apply a compression force to the patient's body and/or limbs to immobilize the patient's body and/or limbs relative to the platform. The polyethylene foam or other cushioning material may reduce or eliminate pressure points on the patient's body that cause discomfort. Ensuring the patient is as comfortable as reasonably possible may further reduce movement of the patient relative to the medical imaging device.

In some embodiments, the straps and/or flaps are positioned and arranged on the platform to allow the straps to apply compression to the patient's body and/or limbs above and/or below the major joints. In some embodiments, the straps and/or flaps are positioned to apply compression above and/or below the knee, the hip, the shoulder, the elbow, the wrist, the ankle, or the neck. For example, a strap or flap that applies compression to the entire leg would apply a greater pressure on the knee (e.g., to the kneecap), which results in discomfort for the patient while also limiting the effectiveness of immobilizing the upper leg and lower leg above and below the knee. By having straps and/or flaps that apply compression to the upper leg and lower leg above and below the knee, the leg is immobilized more securely while limiting discomfort to the patient. In some embodiments, the straps and/or flaps overlap at the joint providing a seam or joint in the straps and/or flaps that allows compression of the main portion of the limbs without creating pressure points at the joints.

The straps and/or flaps may be radiotransparent to allow signal to reach the medical imaging device, as described herein. In some embodiments, the straps and/or flaps are made of or include nylon to provide compression and remain radiotransparent. In some embodiments, the straps and/or flaps are made of or include an elastic material to provide compression while allowing some movement to the patient for comfort. For example, the straps and/or flaps may include a portion that is elastic that allows some movement of the strap and/or flap while the remaining portion of the strap and/or flap is inelastic to provide compression to the patient's body. The straps and/or flaps may include a closure device that is also radiotransparent or positioned on the immobilizer away from (e.g., not overlapping relative to the medical imaging device's receiver) the patient's body. The closure device may be visible in the composite image, but not overlap the patient's body. In some embodiments, the closure device may include a hook-and-loop closure, an adhesive material, a clip, clasp, buckle, or other mechanical closure mechanism.

Figure 3:
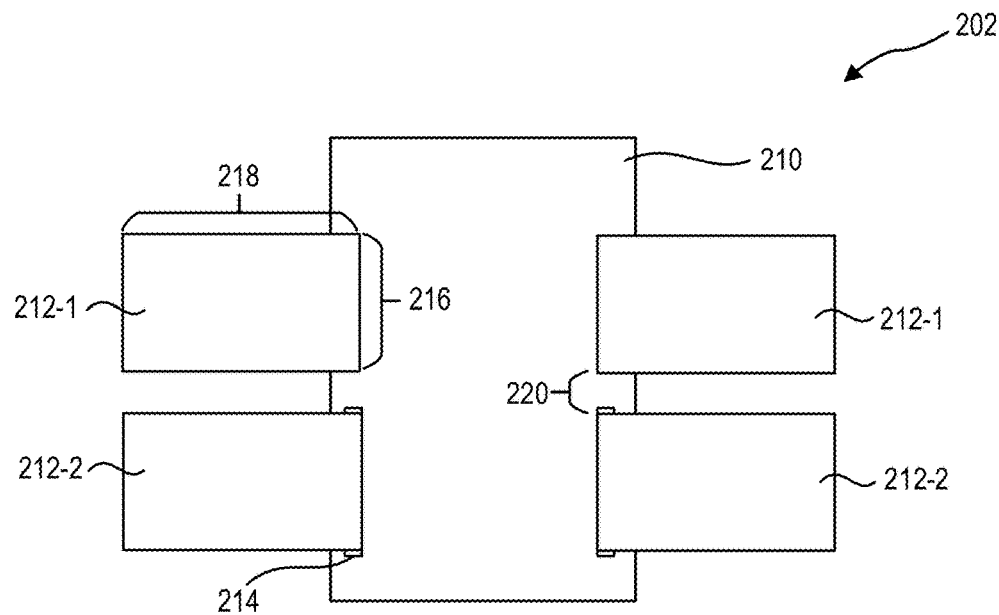
FIG. 3 is a top view of a 2-week immobilizer, according to at least one embodiment of the present disclosure.

FIG. 3 is a schematic representation of an immobilizer for a 2-week-old patient. The immobilizer 202 includes a platform 210 with a plurality of pairs of flaps 212-1, 212-2 connected to the platform. The platform 210 and flaps 212-1, 212-2 are radiotransparent to limit and/or prevent artifacts in the medical imaging signal.

In some embodiments, the flaps 212-1, 212-2 are affixed to the platform 210. For example, the flaps 212-1, 212-2 may be sewn to the platform 210 with radiotransparent thread or wire. In another example, the flaps 212-1, 212-2 may be riveted or screwed to the platform 210 with mechanical fasteners that are radiotransparent. In some embodiments, the flaps 212-1, 212-2 are not fixed to the platform 210, but rather are continuous across a bottom surface (opposite the top view illustrated in FIG. 3) of the platform 210 and pass through apertures 214 or slots in the platform 210 such that the left and right portions of flap 212-1, 212-2 connects the flap 212-1, 212-2 into a continuous loop around both the patient and the platform to compress the patient against the platform 210. In some embodiments, the flaps 212-1, 212-2 pass through apertures 214 or slots in the platform 210 and are secured to the bottom surface of the platform 210 by a mechanical fastener, an adhesive, a hook-and-loop fastener, or other securing mechanism.

Each pair of the flaps 212-1, 212-2 has a flap length 216 in a longitudinal direction and a flap width 218 in a direction transverse to the longitudinal direction. In some embodiments, the flap length 216 is in a range having an upper value, a lower value, or upper and lower values including any of 6 inches (in), 7 in, 8 in, 9 in, 10 in, or any values therebetween. For example, the flap length 216 may be greater than 6 in. In some examples, the flap length 216 may be less than 10 in. In some examples, the flap length 216 may be between 6 in and 10 in. In some examples, the flap length 216 may be between 8 in and 10 in. In at least one example, the flap length 216 is about 9.5 in.

In some embodiments, the flap width 218 of each flap of the pair of flaps 212-1, 212-2 is in a range having an upper value, a lower value, or an upper and lower value including any of 8 in, 9 in, 10 in, 11 in, 12 in, 13 in, 14 in, 15 in, 16 in, or any values therebetween. In some examples, the flap width 218 is greater than 8 in. In some examples, the flap width 218 is less than 16 in. In some examples, the flap width 218 is between 8 in and 16 in. In some examples, the flap width 218 is between 10 in and 14 in. In at least one example, the flap width 218 is about 12 in.

Some embodiments of an immobilizer have pairs of flaps 212-1, 212-2 with space therebetween such that a gap 220 exists between at least two of the pairs of flaps 212-1, 212-2. In some embodiments, a length of the gap 220 in the longitudinal direction is in a range having an upper value, a lower value, or upper and lower values including any of 0.1 in, 0.25 in, 0.5 in, 1.0 in, 2.0 in, or any values therebetween. For example, the length of the gap 220 may be greater than 0.1 in. In some examples, the length of the gap 220 may be less than 2.0 in. In some examples, the length of the gap 220 may be between 0.1 in and 2.0 in. In some examples, the length of the gap 220 may be between 0.5 in and 1.0 in. In at least one example, the length of the gap 220 is about 0.5 in.

Some embodiments of an immobilizer have pairs of flaps 212-1, 212-2 with an overlap therebetween such that an overlap exists with at least two of the pairs of flaps 212-1, 212-2. In some embodiments, a length of the overlap in the longitudinal direction is in a range having an upper value, a lower value, or upper and lower values including any of 0.1 in, 0.25 in, 0.5 in, 1.0 in, 2.0 in, or any values therebetween. For example, the length of the overlap may be greater than 0.1 in. In some examples, the length of the overlap may be less than 2.0 in. In some examples, the length of the overlap may be between 0.1 in and 2.0 in. In some examples, the length of the overlap may be between 0.5 in and 1.0 in. In at least one example, the length of the overlap is about 0.5 in.

As illustrated in FIG. 3, some embodiments of a 2-week immobilizer 202 have no shoulder straps to immobilize the infant's shoulders and neck. As the infant is still developing the musculature to move its neck and head, the shoulder straps only function to reduce the patient's comfort without providing any additional immobilization.

Figure 4:
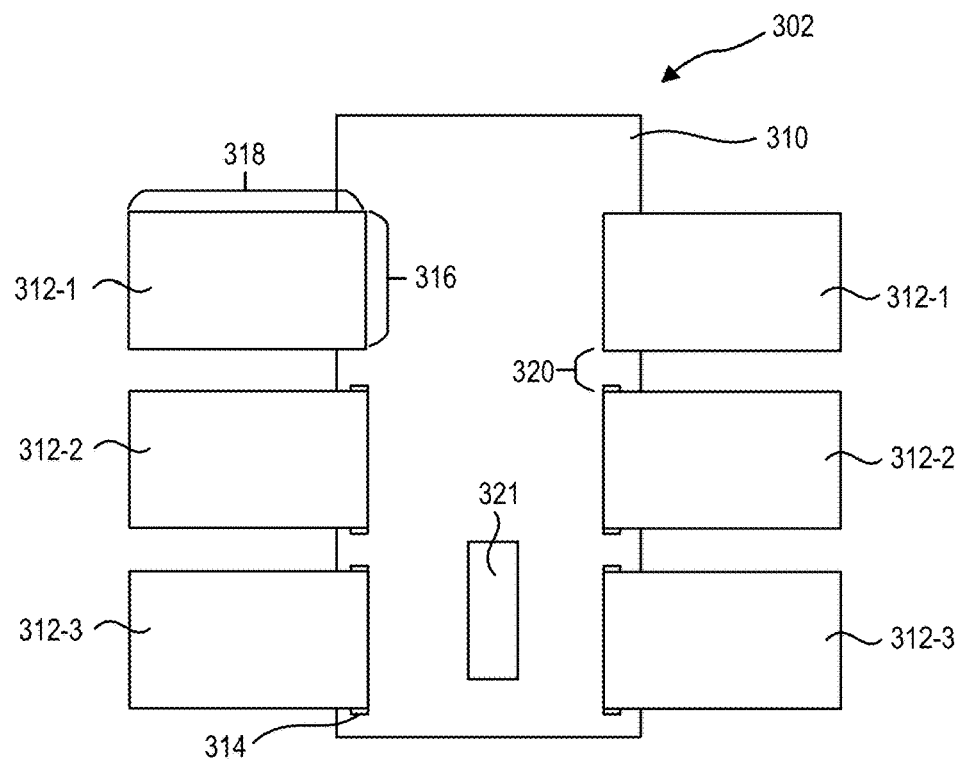
FIG. 4 is a top view of a 6-month immobilizer, according to at least one embodiment of the present disclosure.

FIG. 4 is a schematic representation of an immobilizer for a 6-month-old patient. The immobilizer 302 includes a platform 310 with a plurality of pairs of flaps 312-1, 312-2, 312-3 connected to the platform. The platform 310 and flaps 312-1, 312-2, 312-3 are radiotransparent to limit and/or prevent artifacts in the medical imaging signal.

In some embodiments, the flaps 312-1, 312-2, 312-3 are affixed to the platform 310. For example, the flaps 312-1, 312-2, 312-3 may be sewn to the platform 310 with radiotransparent thread or wire. In another example, the flaps 312-1, 312-2, 312-3 may be riveted or screwed to the platform 310 with mechanical fasteners that are radiotransparent. In some embodiments, the flaps 312-1, 312-2, 312-3 are not fixed to the platform 310, but rather are continuous across a bottom surface (opposite the top view illustrated in FIG. 4) of the platform 310 and pass through apertures 314 or slots in the platform 310 such that the left and right portions of flap 312-1, 312-2, 312-3 connects the flap 312-1, 312-2, 312-3 into a continuous loop around both the patient and the platform to compress the patient against the platform 310. In some embodiments, the flaps 312-1, 312-2, 312-3 pass through apertures 314 or slots in the platform 310 and are secured to the bottom surface of the platform 310 by a mechanical fastener, an adhesive, a hook-and-loop fastener, or other securing mechanism.

Each pair of the flaps 312-1, 312-2, 312-3 has a flap length 316 in a longitudinal direction and a flap width 318 in a direction transverse to the longitudinal direction. In some embodiments, the flap length 316 is in a range having an upper value, a lower value, or upper and lower values including any of 6 in, 7 in, 8 in, 9 in, 10 in, 11 in, 12 in, or any values therebetween. For example, the flap length 316 may be greater than 6 in. In some examples, the flap length 316 may be less than 12 in. In some examples, the flap length 316 may be between 6 in and 12 in. In some examples, the flap length 316 may be between 9 in and 11 in. In at least one example, the flap length 316 is about 10.5 in.

In some embodiments, the flap length 316 varies between pairs of flaps 312-1, 312-2, 312-3. For example, the first pair of flaps 312-1 may have a flap length that is greater than the flap length of the second pair of flaps 312-2. In some examples, the first pair of flaps 312-1 may have a flap length that is greater than the flap length of the third pair of flaps 312-3. In some examples, the second pair of flaps 312-2 may have a flap length that is less than the flap length of the third pair of flaps 312-3. In at least one example, the first pair of flaps 312-1 may have a flap length that is greater than the flap length of the second pair of flaps 312-2 and the third pair of flaps 312-3, and the flap length of the second pair of flaps 312-2 and the third pair of flaps 312-3 may be the same.

In some embodiments, the flap width 318 of each flap of the pair of flaps 312-1, 312-2, 312-3 is in a range having an upper value, a lower value, or an upper and lower value including any of 10 in, 11 in, 12 in, 13 in, 14 in, 15 in, 16 in, 17 in, 18 in, or any values therebetween. In some examples, the flap width 318 is greater than 10 in. In some examples, the flap width 318 is less than 18 in. In some examples, the flap width 318 is between 10 in and 18 in. In some examples, the flap width 318 is between 12 in and 16 in. In at least one example, the flap width 318 is about 14 in.

In some embodiments, the flap width 318 varies between pairs of flaps 312-1, 312-2, 312-3. For example, the first pair of flaps 312-1 may have a flap width that is greater than the flap width of the second pair of flaps 312-2. In some examples, the first pair of flaps 312-1 may have a flap width that is greater than the flap width of the third pair of flaps 312-3. In some examples, the second pair of flaps 312-2 may have a flap width that is less than the flap width of the third pair of flaps 312-3. In at least one example, the first pair of flaps 312-1 may have a flap width that is greater than the flap width of the second pair of flaps 312-2 and the third pair of flaps 312-3, and the flap width of the second pair of flaps 312-2 may be less than a flap width of the third pair of flaps 312-3.

Some embodiments of an immobilizer have pairs of flaps 312-1, 312-2, 312-3 with space therebetween such that a gap 320 exists between at least two of the pairs of flaps 312-1, 312-2, 312-3. In some embodiments, a length of the gap 320 in the longitudinal direction is in a range having an upper value, a lower value, or upper and lower values including any of 0.1 in, 0.25 in, 0.5 in, 1.0 in, 2.0 in, or any values therebetween. For example, the length of the gap 320 may be greater than 0.1 in. In some examples, the length of the gap 320 may be less than 2.0 in. In some examples, the length of the gap 320 may be between 0.1 in and 2.0 in. In some examples, the length of the gap 320 may be between 0.5 in and 1.0 in. In at least one example, the length of the gap 320 is about 0.5 in.

Some embodiments of an immobilizer have pairs of flaps 312-1, 312-2, 312-3 with an overlap therebetween such that an overlap exists with at least two of the pairs of flaps 312-1, 312-2, 312-3. In some embodiments, a length of the overlap in the longitudinal direction is in a range having an upper value, a lower value, or upper and lower values including any of 0.1 in, 0.25 in, 0.5 in, 1.0 in, 2.0 in, or any values therebetween. For example, the length of the overlap may be greater than 0.1 in. In some examples, the length of the overlap may be less than 2.0 in. In some examples, the length of the overlap may be between 0.1 in and 2.0 in. In some examples, the length of the overlap may be between 0.5 in and 1.5 in. In at least one example, the length of the overlap is about 1.25 in. In a particular example, the length of the overlap between the first pair of flaps 312-1 and the second pair of flaps 312-2 is 1.25 in, and there is no overlap between the second pair of flaps 312-2 and the third pair of flaps 312-3. The immobilizer 302 may include a leg support 321 to stabilize, support, and separate the legs, improving the image quality of the collected signal from the lower portion of the body.

As illustrated in FIG. 4, some embodiments of a 6-month immobilizer 302 have no shoulder straps to immobilize the infant's shoulders and neck. As the infant is still developing the musculature to move its neck and head, the shoulder straps only function to reduce the patient's comfort without providing any additional immobilization.

Figure 5:
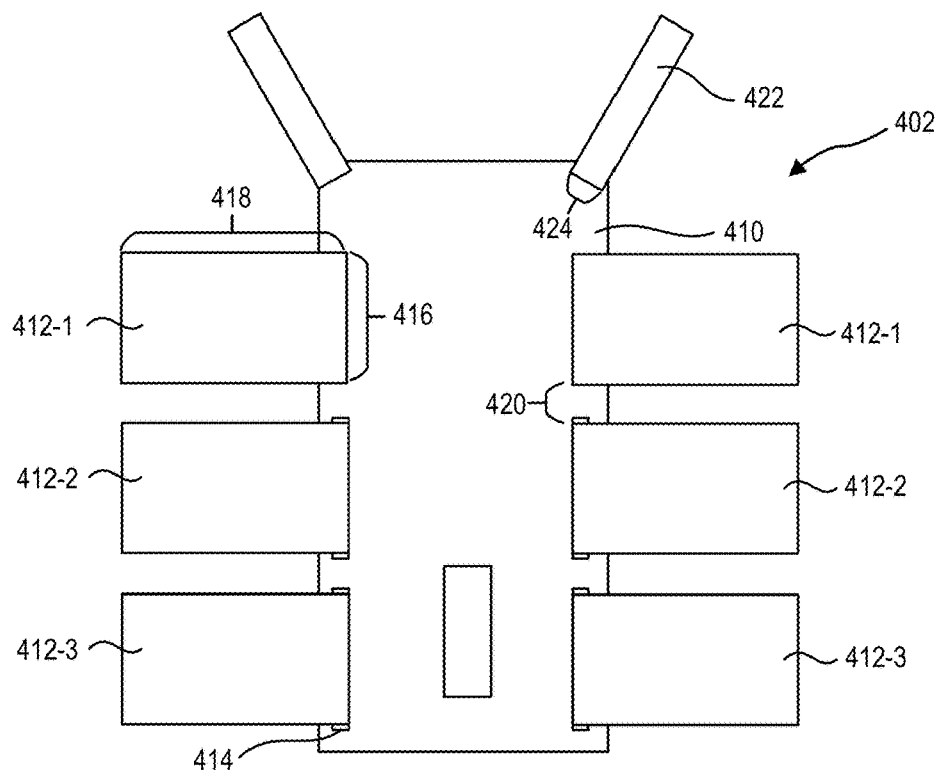
FIG. 5 is a top view of a 12-month immobilizer, according to at least one embodiment of the present disclosure.

FIG. 5 is a schematic representation of an immobilizer for a 12-month-old patient. The immobilizer 402 includes a platform 410 with a plurality of pairs of flaps 412-1, 412-2, 412-3 connected to the platform 410. The platform 410 and flaps 412-1, 412-2, 412-3 are radiotransparent to limit and/or prevent artifacts in the medical imaging signal.

In some embodiments, the flaps 412-1, 412-2, 412-3 are affixed to the platform 410. For example, the flaps 412-1, 412-2, 412-3 may be sewn to the platform 410 with radiotransparent thread or wire. In another example, the flaps 412-1, 412-2, 412-3 may be riveted or screwed to the platform 410 with mechanical fasteners that are radiotransparent. In some embodiments, the flaps 412-1, 412-2, 412-3 are not fixed to the platform 410, but rather are continuous across a bottom surface (opposite the top view illustrated in FIG. 5) of the platform 410 and pass through apertures 414 or slots in the platform 410 such that the left and right portions of flap 412-1, 412-2, 412-3 connects the flap 412-1, 412-2, 412-3 into a continuous loop around both the patient and the platform to compress the patient against the platform 410. In some embodiments, the flaps 412-1, 412-2, 412-3 pass through apertures 414 or slots in the platform 410 and are secured to the bottom surface of the platform 410 by a mechanical fastener, an adhesive, a hook-and-loop fastener, or other securing mechanism.

Each pair of the flaps 412-1, 412-2, 412-3 has a flap length 416 in a longitudinal direction and a flap width 418 in a direction transverse to the longitudinal direction. In some embodiments, the flap length 416 is in a range having an upper value, a lower value, or upper and lower values including any of 6 in, 7 in, 8 in, 9 in, 10 in, 11 in, 12 in, 13 in, 14 in, or any values therebetween. For example, the flap length 416 may be greater than 6 in. In some examples, the flap length 416 may be less than 14 in. In some examples, the flap length 416 may be between 6 in and 13.5 in. In some examples, the flap length 416 may be between 9 in and 13 in. In at least one example, the flap length 416 is about 12.75 in.

In some embodiments, the flap length 416 varies between pairs of flaps 412-1, 412-2, 412-3. For example, the first pair of flaps 412-1 may have a flap length 416 that is less than the flap length 416 of the second pair of flaps 412-2. In some examples, the first pair of flaps 412-1 may have a flap length 416 that is greater than the flap length 416 of the third pair of flaps 412-3. In some examples, the second pair of flaps 412-2 may have a flap length 416 that is greater than the flap length 416 of the third pair of flaps 412-3. In at least one example, the first pair of flaps 412-1 may have a flap length 416 that is less than the flap length of the second pair of flaps 412-2 and greater than the third pair of flaps 412-3, and the flap length 416 of the second pair of flaps 412-2 may be greater than the flap length 416 of the third pair of flaps 412-3.

In some embodiments, the flap width 418 of each flap of the pair of flaps 412-1, 412-2, 412-3 is in a range having an upper value, a lower value, or an upper and lower value including any of 10 in, 11 in, 12 in, 13 in, 14 in, 15 in, 16 in, 17 in, 18 in, or any values therebetween. In some examples, the flap width 418 is greater than 10 in. In some examples, the flap width 418 is less than 18 in. In some examples, the flap width 418 is between 10 in and 18 in. In some examples, the flap width 418 is between 12 in and 16 in. In at least one example, the flap width 418 is about 14 in.

In some embodiments, the flap width 418 varies between pairs of flaps 412-1, 412-2, 412-3. For example, the first pair of flaps 412-1 may have a flap width 418 that is greater than the flap width 418 of the second pair of flaps 412-2. In some examples, the first pair of flaps 412-1 may have a flap width 418 that is greater than the flap width of the third pair of flaps 412-3. In some examples, the second pair of flaps 412-2 may have a flap width 418 that is less than the flap width 418 of the third pair of flaps 412-3. In at least one example, the first pair of flaps 412-1 may have a flap width 418 that is greater than the flap width 418 of the second pair of flaps 412-2 and the third pair of flaps 412-3, and the flap width 418 of the second pair of flaps 412-2 may be less than a flap width 418 of the third pair of flaps 412-3.

Some embodiments of an immobilizer have pairs of flaps 412-1, 412-2, 412-3 with space therebetween such that a gap 420 exists between at least two of the pairs of flaps 412-1, 412-2, 412-3. In some embodiments, a length of the gap 420 in the longitudinal direction is in a range having an upper value, a lower value, or upper and lower values including any of 0.1 in, 0.25 in, 0.5 in, 1.0 in, 2.0 in, or any values therebetween. For example, the length of the gap 420 may be greater than 0.1 in. In some examples, the length of the gap 420 may be less than 2.0 in. In some examples, the length of the gap 420 may be between 0.1 in and 2.0 in. In some examples, the length of the gap 420 may be between 0.5 in and 1.0 in. In at least one example, the length of the gap 420 is about 0.5 in.

Some embodiments of an immobilizer have pairs of flaps 412-1, 412-2, 412-3 with an overlap therebetween such that an overlap exists with at least two of the pairs of flaps 412-1, 412-2, 412-3. In some embodiments, a length of the overlap in the longitudinal direction is in a range having an upper value, a lower value, or upper and lower values including any of 0.1 in, 0.25 in, 0.5 in, 1.0 in, 2.0 in, or any values therebetween. For example, the length of the overlap may be greater than 0.1 in. In some examples, the length of the overlap may be less than 2.0 in. In some examples, the length of the overlap may be between 0.1 in and 2.0 in. In some examples, the length of the overlap may be between 0.5 in and 1.5 in. In at least one example, the length of the overlap is about 1.25 in. In a particular example, the length of the overlap between the first pair of flaps 412-1 and the second pair of flaps 412-2 is 1.25 in, and there is no overlap between the second pair of flaps 412-2 and the third pair of flaps 412-3.

The 12-month immobilizer 402 includes shoulder straps 422 that connect to an edge of the platform 410 proximate the first pair of flaps 412-1. The shoulder straps 422 have a strap width 424 in a range having an upper value, a lower value, or upper and lower values including any of 1 in, 2 in, 3 in, 4 in, 5 in, or any values therebetween. For example, the strap width 424 may be greater than 1 in. In some examples, the strap width 424 may be less than 5 in. In some examples, the strap width 424 is between 1 in and 5 in. In some examples, the strap width 424 is between 2 in and 4 in. In some examples, the strap width 424 is about 3 in.

Figure 6:
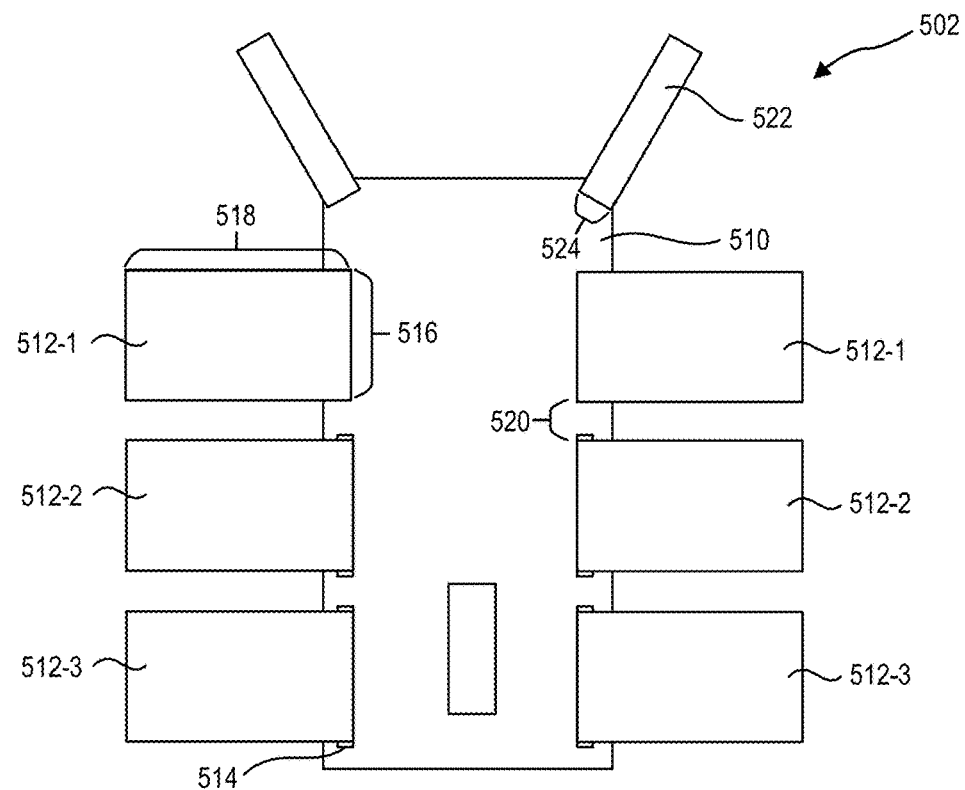
FIG. 6 is top view of a 24-month immobilizer, according to at least one embodiment of the present disclosure.

FIG. 6 is a schematic representation of an immobilizer for a 24-month-old patient. The immobilizer 502 includes a platform 510 with a plurality of pairs of flaps 512-1, 512-2, 512-3 connected to the platform 510. The platform 510 and flaps 512-1, 512-2, 512-3 are radiotransparent to limit and/or prevent artifacts in the medical imaging signal.

In some embodiments, the flaps 512-1, 512-2, 512-3 are affixed to the platform 510. For example, the flaps 512-1, 512-2, 512-3 may be sewn to the platform 510 with radiotransparent thread or wire. In another example, the flaps 512-1, 512-2, 512-3 may be riveted or screwed to the platform 510 with mechanical fasteners that are radiotransparent. In some embodiments, the flaps 512-1, 512-2, 512-3 are not fixed to the platform 510, but rather are continuous across a bottom surface (opposite the top view illustrated in FIG. 6) of the platform 510 and pass through apertures 514 or slots in the platform 510 such that the left and right portions of flap 512-1, 512-2, 512-3 connects the flap 512-1, 512-2, 512-3 into a continuous loop around both the patient and the platform to compress the patient against the platform 510. In some embodiments, the flaps 512-1, 512-2, 512-3 pass through apertures 514 or slots in the platform 510 and are secured to the bottom surface of the platform 510 by a mechanical fastener, an adhesive, a hook-and-loop fastener, or other securing mechanism.

Each pair of the flaps 512-1, 512-2, 512-3 has a flap length 516 in a longitudinal direction and a flap width 518 in a direction transverse to the longitudinal direction. In some embodiments, the flap length 516 is in a range having an upper value, a lower value, or upper and lower values including any of 6 in, 7 in, 8 in, 9 in, 10 in, 11 in, 12 in, 13 in, 14 in, or any values therebetween. For example, the flap length 516 may be greater than 6 in. In some examples, the flap length 516 may be less than 14 in. In some examples, the flap length 516 may be between 6 in and 13.5 in. In some examples, the flap length 516 may be between 9 in and 13 in. In at least one example, the flap length 516 is about 12.75 in.

In some embodiments, the flap length 516 varies between pairs of flaps 512-1, 512-2, 512-3. For example, the first pair of flaps 512-1 may have a flap length 516 that is less than the flap length 516 of the second pair of flaps 512-2. In some examples, the first pair of flaps 512-1 may have a flap length 516 that is greater than the flap length 516 of the third pair of flaps 512-3. In some examples, the second pair of flaps 512-2 may have a flap length 516 that is greater than the flap length 516 of the third pair of flaps 512-3. In at least one example, the first pair of flaps 512-1 may have a flap length 516 that is less than the flap length 516 of the second pair of flaps 512-2 and greater than the third pair of flaps 512-3, and the flap length 516 of the second pair of flaps 512-2 may be greater than the flap length 516 of the third pair of flaps 512-3.

In some embodiments, the flap width 518 of each flap of the pair of flaps 512-1, 512-2, 512-3 is in a range having an upper value, a lower value, or an upper and lower value including any of 10 in, 11 in, 12 in, 13 in, 14 in, 15 in, 16 in, 17 in, 18 in, or any values therebetween. In some examples, the flap width 518 is greater than 10 in. In some examples, the flap width 518 is less than 18 in. In some examples, the flap width 518 is between 10 in and 18 in. In some examples, the flap width 518 is between 12 in and 16 in. In at least one example, the flap width 518 is about 14 in.

In some embodiments, the flap width 518 varies between pairs of flaps 512-1, 512-2, 512-3. For example, the first pair of flaps 512-1 may have a flap width 518 that is greater than the flap width 518 of the second pair of flaps 512-2. In some examples, the first pair of flaps 512-1 may have a flap width 518 that is greater than the flap width of the third pair of flaps 512-3. In some examples, the second pair of flaps 512-2 may have a flap width 518 that is less than the flap width 518 of the third pair of flaps 512-3. In at least one example, the first pair of flaps 512-1 may have a flap width 518 that is greater than the flap width 518 of the second pair of flaps 512-2 and the third pair of flaps 512-3, and the flap width 518 of the second pair of flaps 512-2 may be less than a flap width 518 of the third pair of flaps 512-3.

Some embodiments of an immobilizer have pairs of flaps 512-1, 512-2, 512-3 with space therebetween such that a gap 520 exists between at least two of the pairs of flaps 512-1, 512-2, 512-3. In some embodiments, a length of the gap 520 in the longitudinal direction is in a range having an upper value, a lower value, or upper and lower values including any of 0.1 in, 0.25 in, 0.5 in, 1.0 in, 2.0 in, or any values therebetween. For example, the length of the gap 520 may be greater than 0.1 in. In some examples, the length of the gap 520 may be less than 2.0 in. In some examples, the length of the gap 520 may be between 0.1 in and 2.0 in. In some examples, the length of the gap 520 may be between 0.5 in and 1.0 in. In at least one example, the length of the gap 520 is about 0.5 in.

Some embodiments of an immobilizer have pairs of flaps 512-1, 512-2, 512-3 with an overlap therebetween such that an overlap exists with at least two of the pairs of flaps 512-1, 512-2, 512-3. In some embodiments, a length of the overlap in the longitudinal direction is in a range having an upper value, a lower value, or upper and lower values including any of 0.1 in, 0.25 in, 0.5 in, 1.0 in, 2.0 in, or any values therebetween. For example, the length of the overlap may be greater than 0.1 in. In some examples, the length of the overlap may be less than 2.0 in. In some examples, the length of the overlap may be between 0.1 in and 2.0 in. In some examples, the length of the overlap may be between 0.5 in and 1.5 in. In at least one example, the length of the overlap is about 1.25 in. In a particular example, the length of the overlap between the first pair of flaps 512-1 and the second pair of flaps 512-2 is 1.25 in, and there is no overlap between the second pair of flaps 512-2 and the third pair of flaps 512-3.

The 24-month immobilizer 502 includes shoulder straps 522 that connect to an edge of the platform 510 proximate the first pair of flaps 512-1. The shoulder straps 522 have a strap width 524 in a range having an upper value, a lower value, or upper and lower values including any of 1 in, 2 in, 3 in, 4 in, 5 in, or any values therebetween. For example, the strap width 524 may be greater than 1 in. In some examples, the strap width 524 may be less than 5 in. In some examples, the strap width 524 is between 1 in and 5 in. In some examples, the strap width 524 is between 2 in and 4 in. In some examples, the strap width 524 is about 3 in.

In some embodiments, a leg stabilizer 526 is positioned on and/or fixed to the platform 510 between the second pair of flaps 512-2 and/or the third pair of flaps 512-3. The leg stabilizer 526 may be positioned between the patient's legs to provide support and comfort during the imaging procedure, as well as provide separation between the patient's legs for distinct imaging of the composition of the legs. In some embodiments, the leg stabilizer 526 includes or is made of the cushion material.

Figure 7:
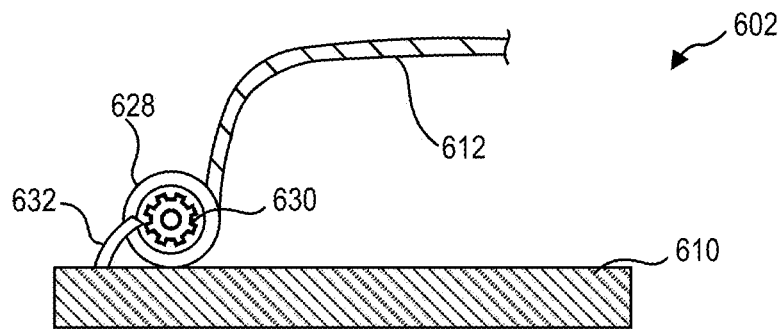
FIG. 7 is an end cross-sectional view of an adjustable tensioning mechanism, according to at least one embodiment of the present disclosure.

FIG. 7 is an end view of a flap 612 connected to a platform 610 through an adjustable tensioning mechanism 628. In some embodiments, the clinician fastens the flaps of a pair of flaps to one another to compress the patient's body against the platform 610. In some embodiments, an adjustable tensioning mechanism 628 allows the compression force of the flap 612 to change after the pair of flaps are connected or fastened to one another. For example, the adjustable tensioning mechanism 628 may include a ratcheting mechanism 630 with a movable pawl 632. The ratcheting mechanism 630 may allow the flaps 612 to be drawn tighter and resist loosening during the medical imaging procedure. The movable pawl 632 may be selectively disengaged from the ratcheting mechanism 630 to release force on the adjustable tensioning mechanism 628 and, thereby, tension on the flaps 612. Releasing tension after the medical imaging system (such as the medical imaging system 100 described in relation to FIG. 1 and FIG. 2) has completed imaging the associated portion of the patient's body may lessen discomfort related to the restraint of the immobilizer.

Figure 8:
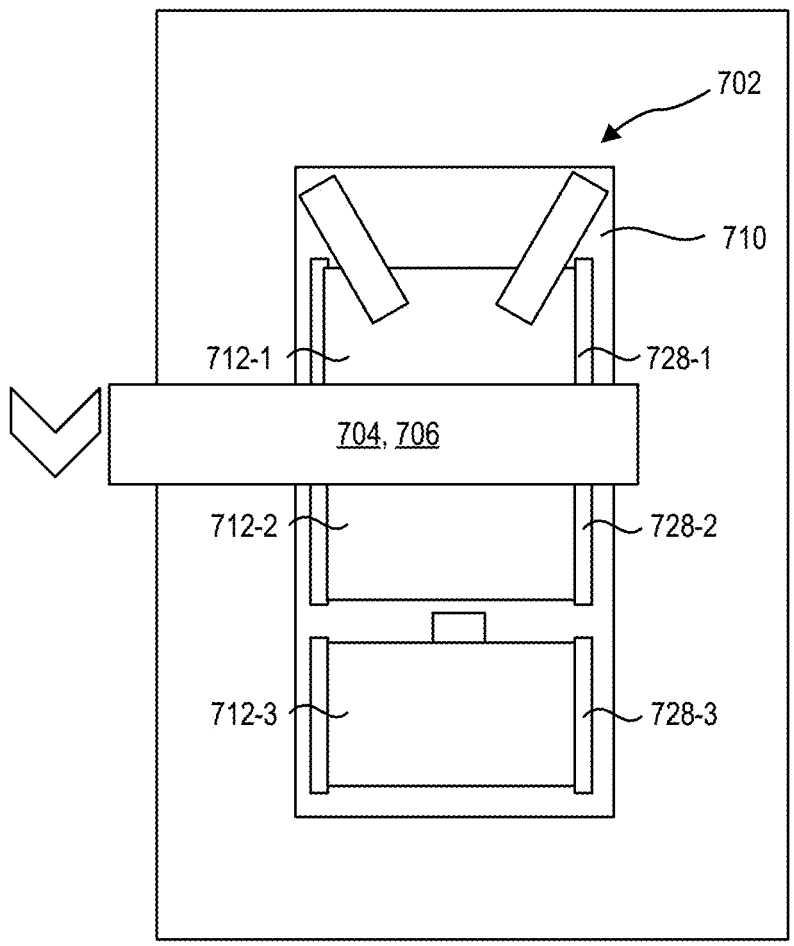
FIG. 8 is a top view of an immobilizer with adjustable tensioning mechanisms, according to at least one embodiment of the present disclosure.

In one example, such as illustrated in FIG. 8, one or more adjustable tensioning mechanisms 728-1, 728-2, 728-3 may allow for a coordinated tensioning and/or de-tensioning of the flaps 712-1, 712-2, 712-3 of the immobilizer 702 based at least partially on the movement or position of the movable energy source 704 and/or a movable signal receiver 706 relative to the immobilizer 702. As the movable energy source 704 and/or a movable signal receiver 706 moves relative to the immobilizer 702, a controller or a clinician may adjust the one or more adjustable tensioning mechanism 728-1, 728-2, 728-3 to change the tension of the flaps 712-1, 712-2, 712-3 to ensure the patient is effectively immobilized at the location of the movable energy source 704 and/or a movable signal receiver 706 for imaging, while the patient is able to move at other positions along their body.

One or more specific embodiments of the present disclosure are described herein. These described embodiments are examples of the presently disclosed techniques. Additionally, in an effort to provide a concise description of these embodiments, not all features of an actual embodiment may be described in the specification. It should be appreciated that in the development of any such actual implementation, as in any engineering or design project, numerous embodiment-specific decisions will be made to achieve the developers' specific goals, such as compliance with system-related and business-related constraints, which may vary from one embodiment to another. Moreover, it should be appreciated that such a development effort might be complex and time consuming, but would nevertheless be a routine undertaking of design, fabrication, and manufacture for those of ordinary skill having the benefit of this disclosure.

The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. For example, any element described in relation to an embodiment herein may be combinable with any element of any other embodiment described herein. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

The terms "approximately," "about," and "substantially" as used herein represent an amount close to the stated amount that still performs a desired function or achieves a desired result. For example, the terms "approximately," "about," and "substantially" may refer to an amount that is within less than 5% of, within less than 1% of, within less than 0.1% of, and within less than 0.01% of a stated amount. Further, it should be understood that any directions or reference frames in the preceding description are merely relative directions or movements. For example, any references to "up" and "down" or "above" or "below" are merely descriptive of the relative position or movement of the related elements.

The present disclosure may be embodied in other specific forms without departing from its spirit or characteristics. The described embodiments are to be considered as illustrative and not restrictive. The scope of the disclosure is, therefore, indicated by the appended claims rather than by the foregoing description. Changes that come within the meaning and range of equivalency of the claims are to be embraced within their scope.

What is claimed is:

1. A medical imaging support, the support comprising:
a substantially flat radiotransparent platform having a longitudinal direction between a top edge of the radiotransparent platform and a bottom edge of the radiotransparent platform;
a plurality of sets of radiotransparent flaps where a first set of radiotransparent flaps is positioned closer to the top edge in the longitudinal direction than a second set of radiotransparent flaps, wherein at least one set of radiotransparent flaps includes a first flap and a second flap where the first flap is fixed to the platform proximate a first side edge of the platform and the second flap is fixed to the platform proximate a second side edge of the platform and wherein the first set of radiotransparent flaps overlaps the second set of radiotransparent flaps in the longitudinal direction; and
a closure mechanism positioned on the first flap or second flap of each set of radiotransparent flaps, wherein the closure mechanism selectively fixes the first flap to the second flap of each set of radiotransparent flaps.

2. The support of claim 1, wherein the radiotransparent platform is configured to connect to an imaging device to prevent movement of the support in the vertical plane.

3. The support of claim 1, wherein the first set overlaps the second set by at least 0.25 inches.

4. The support of claim 1, wherein the first flap of the first set of radiotransparent flaps is fixed to the platform at least 1 inch from the first side edge.

5. The support of claim 1, wherein the closure mechanism is a hook and loop closure with a hook material positioned on the first flap and a loop material positioned on the second flap.

6. The support of claim 1, wherein the closure mechanism is a buckle closure.

7. The support of claim 1, wherein the closure mechanism is radiotransparent.

8. The support of claim 1, further comprising at least 3 sets of radiotransparent flaps.

9. The support of claim 1, further comprising a leg stabilizer fixed to the platform between the second set of radiotransparent flaps.

10. The support of claim 1, wherein the first set of radiotransparent flaps is fixed to the platform at least 1 inch from the top edge.

11. The support of claim 1, wherein the second set of radiotransparent flaps is fixed to the platform at least 1 inch from the bottom edge.

12. The support of claim 1, wherein the first flap of the first set is fixed to the platform at least 6 inches from the second flap of the first set.

13. The support of claim 1, further comprising a set of shoulder straps fixed to the platform proximate the top edge.

14. The support of claim 13, a first strap of the set of shoulder straps being fixed to a bottom surface of the platform proximate the top edge and a second strap of the set of shoulder straps being fixed to a bottom surface of the platform proximate the top edge.

15. The support of claim 14, wherein the shoulder straps are non-elastic.

16. The support of claim 1, wherein the radiotransparent flaps of the plurality of radiotransparent flaps are non-elastic.

17. A medical imaging support, the support comprising:
a substantially flat radiotransparent platform having a longitudinal direction between a top edge of the radiotransparent platform and a bottom edge of the radiotransparent platform;
a plurality of sets of radiotransparent flaps where a first set of radiotransparent flaps is positioned closer to the top edge in the longitudinal direction than a second set of radiotransparent flaps, wherein at least one set of radiotransparent flaps is a single piece of radiotransparent material where the first flap is a first end of the single piece of radiotransparent material and the second flap is a second end of the single piece of radiotransparent material and wherein the first set of radiotransparent flaps overlaps the second set of radiotransparent flaps in the longitudinal direction; and
a closure mechanism positioned on the first flap or second flap of each set of radiotransparent flaps, wherein the closure mechanism selectively fixes the first flap to the second flap of each set of radiotransparent flaps.

18. The support of claim 17, wherein the single piece of radiotransparent material is affixed to the platform on a bottom surface of the platform.

19. A medical imaging support, the support comprising:
a substantially flat radiotransparent platform having a longitudinal direction between a top edge of the radiotransparent platform and a bottom edge of the radiotransparent platform;
a plurality of sets of radiotransparent flaps where a first set of radiotransparent flaps is positioned closer to the top edge in the longitudinal direction than a second set of radiotransparent flaps, wherein at least one set of radiotransparent flaps includes a first flap and a second flap where the first flap is fixed to the platform proximate a first side edge of the platform and the second flap is fixed to the platform proximate a second side edge of the platform and wherein the first set of radiotransparent flaps overlaps the second set of radiotransparent flaps in the longitudinal direction;
a closure mechanism positioned on the first flap or second flap of each set of radiotransparent flaps, wherein the closure mechanism selectively fixes the first flap to the second flap of each set of radiotransparent flaps; and
an adjustable tensioning mechanism affixed to at least one flap configured to adjust a tension on the at least one flap.

20. The support of claim 19, wherein the adjustable tensioning mechanism includes a ratcheting mechanism with a selectively engageable pawl.

* * * * *